United States Patent [19]
van der Linden et al.

[11] Patent Number: 5,134,993
[45] Date of Patent: Aug. 4, 1992

[54] INHALATOR DEVICE, IN PARTICULAR A POCKET INHALATOR

[75] Inventors: Klaus van der Linden, Kronach; Juergen Friedrich, Neuensorg; Bernd Zierenberg, Bingen, all of Fed. Rep. of Germany

[73] Assignees: Siemens Aktiengesellschaft, Munich; Boehringer Ingelheim KG, Ingelheim am Rheim, both of Fed. Rep. of Germany

[21] Appl. No.: 449,705

[22] Filed: Dec. 11, 1989

[30] Foreign Application Priority Data

Dec. 13, 1988 [EP] European Pat. Off. ......... 88120823.5

[51] Int. Cl.⁵ ............................................. A61M 11/00
[52] U.S. Cl. ........................... 128/200.14; 128/200.16; 128/200.23
[58] Field of Search ...................... 128/200.14, 200.16, 128/200.23

[56] References Cited

U.S. PATENT DOCUMENTS

| | | | |
|---|---|---|---|
| 4,094,317 | 6/1978 | Wasnich | 128/200.16 |
| 4,109,863 | 8/1978 | Olson et al. | 239/102 |
| 4,113,809 | 9/1978 | Abair et al. | 128/200.16 |
| 4,877,989 | 10/1989 | Drews | 128/200.16 |
| 4,976,259 | 12/1990 | Higson et al. | 128/200.16 |

FOREIGN PATENT DOCUMENTS

| | | |
|---|---|---|
| 531640 | 9/1954 | Belgium . |
| 0258637 | 3/1988 | European Pat. Off. . |
| 1103522 | 3/1961 | Fed. Rep. of Germany . |
| 2524862 | 12/1975 | Fed. Rep. of Germany . |
| 3339180 | 5/1985 | Fed. Rep. of Germany . |
| 2285930 | 4/1976 | France . |
| 2444504 | 7/1980 | France . |

*Primary Examiner*—Edgar S. Burr
*Assistant Examiner*—Aaron J. Lewis
*Attorney, Agent, or Firm*—Herbert L. Lerner; Laurence A. Greenberg

[57] ABSTRACT

An inhalator device includes a housing in which an ultrasonic atomizer is disposed. A device delivers a medication to the ultrasonic atomizer. A mouthpiece is disposed downstream of the ultrasonic atomizer in flow direction of the medication defining a space between the ultrasonic atomizer and the mouthpiece. The housing has an air inlet opening formed therein communicating with the space downstream of the ultrasonic atomizer.

13 Claims, 1 Drawing Sheet

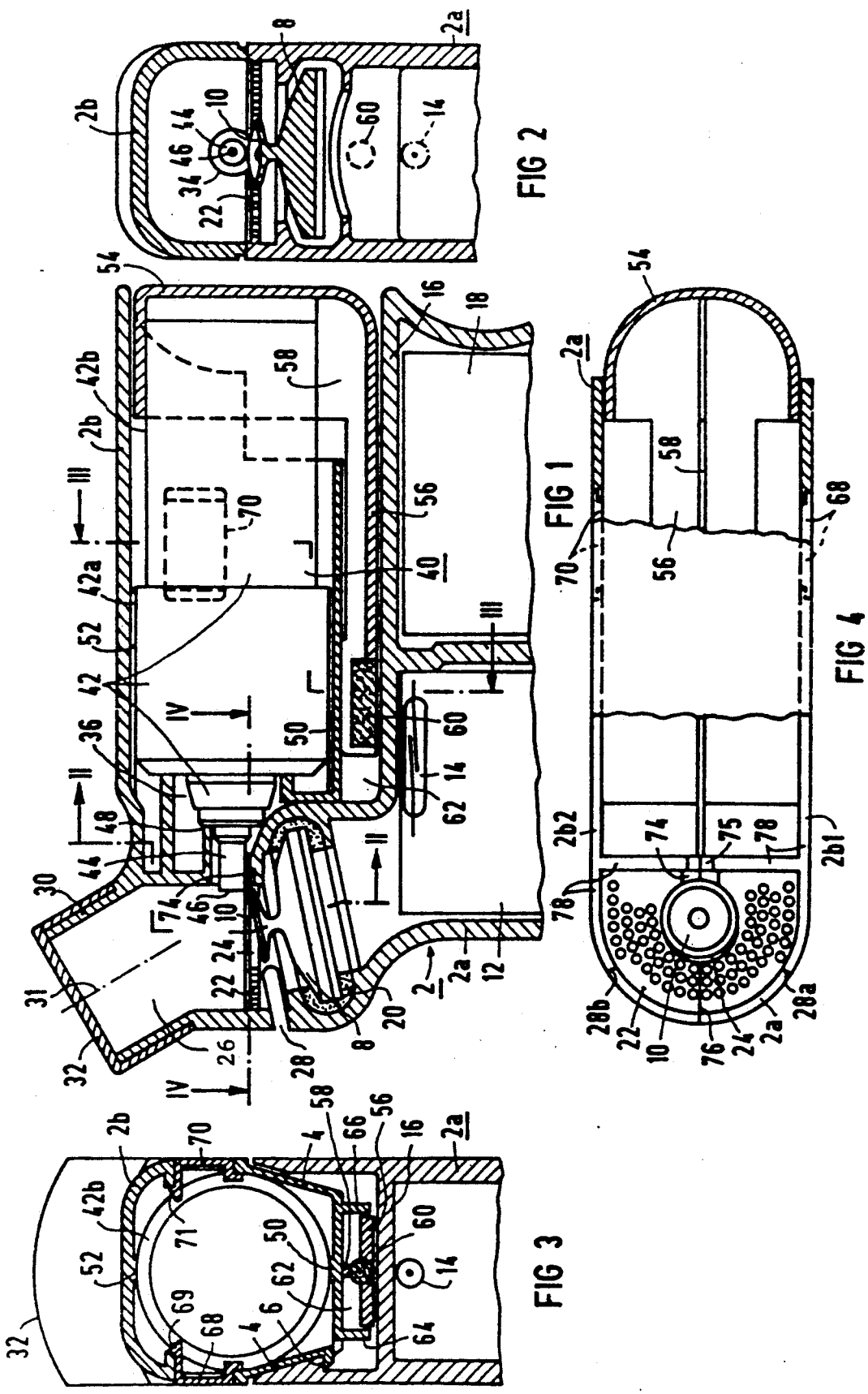

INHALATOR DEVICE, IN PARTICULAR A POCKET INHALATOR

The invention relates to an inhalator device, in particular a pocket inhalator, having a) a housing,
b) an ultrasonic atomizer disposed in the housing,
c) a device for delivering a medication to the ultrasonic atomizer, and
d) a mouthpiece, which adjoins a space downstream of the ultrasonic atomizer.

A pocket inhalator of that type is known from Published European Application No. 0 258 637, for example. The known device is intended for atomizing medicines administered by inhalation. It is constructed in such a way as to produce an aerosol with droplets ranging in diameter substantially from 1 to 5 μm. Thus it is preferentially intended for asthmatics. The preferably plastic housing includes a lower part, which accommodates a piezoelectric vibration system with an atomizer disk, an electronic circuit for ultrasonic excitation of the system, a battery for energy supply to the electronic circuit, and a magnetically actuated switch to turn on the ultrasonic excitation. The housing also includes an upper part, detachably secured to the lower part, with a mouthpiece or suction fitting, in the direction of which the medication is atomized, and a holding chamber into which a medication dosing cartridge can be introduced. The dosing cartridge can be displaced into itself counter to a built-in spring by means of an attached trigger or pushbutton. Upon actuation of the trigger, the cartridge is displaced toward the atomizer disk. At the same time, it is displaced into itself. In that process a droplet is stripped off from the dosing opening of the cartridge onto the atomizer disk. A magnet disposed on the cartridge actuates the switch magnetically when the trigger is pressed, whereupon, after a predetermined period of time, the ultrasonic atomizer with the atomizer disk is excited, after which the stripped-off droplet is atomized. The resultant aerosol can then be inhaled by the user through the mouthpiece. The device can be made small, lightweight and easy to handle and is therefore easy for the user to carry along on any occasion. It can be filled with the medicine to be atomized simply by changing the dosing cartridge.

A dosing cartridge of the type under consideration is known, for instance, from German Published, Non-Examined Application DE-OS 33 39 180. That device has a cylindrical front part, which has a centrally located, a continuous dosage tubule in the end wall thereof, with a dosing opening located on the outside, and a spiral spring in the interior thereof. Protruding into the back of the front portion is a thinner cylindrical back part containing the medicine and having two end walls. When actuated, the back part can slide into the front part. An outlet tubule attached to the end wall located in the interior of the front part is slidingly seated on the back part of the dosing tubule. The dosing cartridge is thus displaceable into itself. If the back part is pressed into the interior of the front part counter to the force of the spring, then a small droplet of the medicine is released through the dosing opening of the dosing tubule.

In the pocket inhalator known from Published European Application No. 0 258 637), it has been found that in the atomizing process some of the aerosol settles on the walls in the aerosol space ahead of the ultrasonic atomizer and/or in the mouthpiece and thus is wasted in terms of the medical treatment. Such settling on the walls is undesirable for various reasons, namely because it is difficult to remove, and there is the danger of damage to the atomizer and the atomizer disk.

It is accordingly an object of the invention to provide an inhalator device, in particular a pocket inhalator, which overcomes the hereinafore-mentioned disadvantages of the heretofore-known devices of this general type and to do so in such a way that the danger of the formation of a film of aerosol on the walls is markedly reduced.

With the foregoing and other objects in view there is provided, in accordance with the invention, an inhalator device, in particular a pocket inhalator, comprising a housing, an ultrasonic atomizer disposed in the housing, a device for delivering a medication to the ultrasonic atomizer, and a mouthpiece disposed downstream of the ultrasonic atomizer in flow direction of the medication defining a space between the ultrasonic atomizer and the mouthpiece, the housing having an air inlet opening formed therein communicating with the space downstream of the ultrasonic atomizer.

Through the use of this air inlet opening, the user can aspirate air into the aerosol space. This air entrains the aerosol located there, so that the probability of its forming a film on the walls is markedly reduced.

In accordance with another feature of the invention, there are provided means disposed between the air inlet opening and the space, through which the air inlet opening communicates with the space, for developing a laminar flow of aspirated air.

In accordance with a further feature of the invention, the laminar flow developing means is in the form of a wall having a multiplicity of small holes formed therein.

The aerosol is entrained by the laminar air flow, making it particularly improbable that the aerosol will settle on the walls before the outlet from the device.

In accordance with an added feature of the invention, the wall is disposed in the immediate vicinity of the ultrasonic atomizer.

In accordance with an additional feature of the invention, the multiplicity of holes formed in the wall are relatively small holes, the wall also has a relatively large opening formed therein, and the ultrasonic atomizer has an atomizer surface protruding into the relatively large opening.

In accordance with again another feature of the invention, the wall is inclined relative to the atomizer surface of the ultrasonic atomizer.

In accordance with again a further feature of the invention, the mouthpiece has an axis, and the wall is disposed in a plane being aligned at an angle of approximately 45° with respect to the axis.

In accordance with again an added feature of the invention, the air inlet opening has the shape of a slit.

In accordance with again an additional feature of the invention, the air inlet opening is disposed above and in the immediate vicinity of the wall.

In accordance with yet another feature of the invention, the wall has an approximately half-ring shape.

In accordance with yet a further feature of the invention, the housing includes a lower part and an upper part detachably secured to the lower part, the device for delivering a medication is disposed in the upper part, the mouthpiece is disposed on the upper part, the air inlet opening is formed in the lower part, and the ultrasonic atomizer and the means for developing a laminar flow of aspirated air are disposed in the lower part.

In accordance with a concomitant feature of the invention, the device for delivering a medication is a dosing cartridge being displaceable into itself and having a front part with a dosing opening formed therein, and preferably there are provided means, such as a stop, for firmly holding the dosing opening in place relative to the ultrasonic atomizer during a dosage operation.

Other features which are considered as characteristic for the invention are set forth in the appended claims.

Although the invention is illustrated and described herein as embodied in an inhalator device, in particular a pocket inhalator, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

FIG. 1 is a fragmentary, diagrammatic, longitudinal-sectional view of a pocket inhalator with an inserted dosing cartridge;

FIG. 2 is a fragmentary sectional view of the device of FIG. 1, taken along the line II—II in FIG. 1, in the direction of the arrows;

FIG. 3 is a fragmentary sectional view of the device of FIG. 1, taken along the line III—III in FIG. 1, in the direction of the arrows; and FIG. 4 is a partly broken-away cross-sectional view of the device of FIG. 1 taken along the line IV—IV in FIG. 1, in the direction of the arrows, with the dosing cartridge and the tongue omitted and the windows removed.

Referring now in detail to the figures of the drawing as a whole, it is seen that the pocket inhalator shown includes a plastic housing 2 with a lower part 2a and an upper part 2b detachably secured thereto. The detachable fastening is assured by means of at least one resilient side wall 4 and a snap-in or detent closure 6.

A piezoelectric vibration system or ultrasonic atomizer 8 with an atomizer disk 10 pointing upward is accommodated on the lower part 2a. The operating frequency of the atomizer 8 is in the range from 1 to 5 MHz. The electrical energy for this is furnished by an electronic circuit 12, which is located in a sealed front chamber. Also accommodated in this chamber is a magnetically actuated switch 14, in particular a reed contact. The reed contact is located on an upper wall 16 or an intermediate wall of the lower part 2a. A replaceable battery 18 is inserted into a rear chamber. The battery supplies electrical energy to the electronic circuit 12. The front and rear chambers are sealed in a fluid-tight manner. To this end, the ultrasonic atomizer 8 in the front chamber is preferably potted, for example with a potting composition 20.

A screen plate or closure wall 22 provided with small, round holes is located in the region of the ultrasonic atomizer 8, specifically in its immediate vicinity. The wall could instead be provided with slits or rectangular openings. The wall 22 is approximately in the form of a half ring. The central portion of the wall 22 has a larger opening 24, into which the atomizer surface of the atomizer disk 10 protrudes. Thus an approximately annular separating gap is formed between the atomizer disk 10 and the rim of the wall 22 defined by the opening 24. The closure wall 22 has two functions: First, it provides mechanical protection of the atomizer 8 and the atomizer disk 10 from damage, and second, because of the many small openings, it acts as means for providing a laminar flow in a space or aerosol space or chamber 26 located above it. As soon as air is aspirated, the laminar flow occurs, through an air inlet opening 28 that communicates with the aerosol space 26 and is preferably constructed as a slit defining slit edges 28a and 28b of the housing 2, as seen in FIG. 4. Thus the wall 22 can be considered as means for creating a laminar flow or laminarizing the aspirated air. Other such means may also be used in this case. The air inlet opening 28 in this case is disposed directly below the wall 22 in the housing 2.

The surface of the atomizer disk 10 is slightly inclined relative to the wall 22, which may also be referred to as a perforated grid. The inclination of the ultrasonic atomizer 8 toward the mouth of the user contributes to a compact construction of the inhalator. At the same time, it provides for atomization in the direction of the outlet opening of the aerosol space 26. Adequate cleaning of the vibrator region is possible because of the holes in the wall 22.

The aerosol space 26 is disposed in the front portion of the top part 2b. The space 26 terminates in a substantially oval mouthpiece 30, the outlet opening of which is closable with a plastic cap 32. The plane of the wall 22 may be aligned at an angle of approximately 45° with respect to the axis 31 of the mouthpiece 30.

The aerosol space 26 communicates through a guide opening 34 with a rear chamber 36, which accommodates a device, generally identified by reference numeral 40, for supplying a medicine to the ultrasonic atomizer 10. The device 40 includes a dosing cartridge 42 which is displaceable into itself and is known per se. The dosing cartridge 42 has a cylindrical front part 42a, and a cylindrical back part 42b which contains the medicine and is displaceable into the part 42a. A dosing tubule 44 acting as a cartridge point and having shoulders at the rear is attached to the front part 42a. A dosing opening is shown at reference numeral 46. When the dosing cartridge 42 is inserted horizontally, the dosing tubule 44 is located in the guide opening 34, leaving an annular gap. Accordingly, the guide opening 34 serves to provide exact positioning. An important feature in this matter is that the point of the dosing cartridge 42 rests with one of the aforementioned shoulders on a stop 48 which, for example, is formed by the wall of the guide opening 34. The stop 48 is important not only for centering but also for firmly holding the dosing cartridge 42 during the dosing process. Centering and guidance are also assured by longitudinal ribs 50, 52 in the chamber 36.

The device 40 for delivering the medication further includes a trigger or plunger 54 attached to the end of the dosing cartridge 42. The trigger 54 is firmly slipped onto the end of the dosing cartridge 42. However, when the dosing cartridge 42 is replaced, it is also readily removable from that end. The dimensioning is selected in such a way that in the undepressed normal position, the rear surface of the trigger 54 approximately closes off the back of the housing 2 and it is introduced further into the upper part 2b upon actuation. The trigger 54 itself thus serves the purpose of exact retention of the cartridge 42.

A comparison of FIG. 1 and FIG. 4 shows that the trigger is constructed as a semicylindrical hollow body. Its lower end wall or lower surface terminates in a tongue 56. In other words the tongue 56 is integral with the trigger 54. The tongue 56 is essentially a rectangular plastic part. It is preferably provided with a longitudinal rib 58 on the upper surface thereof, in order to increase its stability. As will become clear later, the upper edge of the longitudinal rib 58, like the lower surface of the tongue 56, serves as a slide surface, both when the cartridge 42 is inserted and during dosing.

A magnet 60 is secured to the front end of the tongue 56. When the trigger 54 is slipped into place, the tongue 56, the longitudinal rib 58 and the magnet 60 are located in a chamber 62 between the lower part 2a and the upper part 2b. The tongue 56 is longitudinally displaceable in the chamber 62 when the trigger 54 is actuated. There need be no fear of contamination. Upon displacement, the magnet 60 is displaced toward the left relative to the switch 14. If it reaches the sphere of magnetic influence of the switch, the switch 14 is actuated. As a result, ultrasonic excitation of the atomizer 8 is tripped with the aid of the electronic circuit 12, after the trigger 54 is released and upon opening of the switch 14. The tongue 56, longitudinal rib 58 and trigger 54 may be constructed as a single injection molded part. From FIG. 1 it is clear that the magnet 60 which may, for instance, be cylindrical, is let or formed into the tongue 56 and the longitudinal rib 58, and that it is essentially flush with the surface of the tongue 56 oriented toward the switch 54. Upon actuation, the magnet 60 is displaced along the wall 16 of the housing 2. When the user's finger releases the trigger, the cartridge 42 (and thus the magnet 60) returns to its initial position as shown, because of the spring force of the cartridge.

Guidance of the tongue 56 in the chamber 62 is effected with the aid of two side walls 64, 66, which are secured in such a way as to be spaced somewhat apart from and parallel to one another on the lower surface of the upper part 2*b*.

Two windows 68, 70 are disposed one above the other on two parallel longitudinal side walls 2*b*1, 2*b*2 of the upper part 2*b*. The fill level of the cartridge 42, which is made of transparent plastic, can be observed through these windows. The dosing cartridge 42 as shown is in the inserted state between these two windows 68, 70. Preferably the windows 68, 70 are made of plastic and are equipped with detent protrusions 69, 71, so that they can be clipped into suitable openings in the longitudinal side walls of the upper part 2*b*. These detent openings 69, 71 are shaped in such a way that they secure the dosing cartridge 42 against accidentally falling out or being unintentionally removed.

An indentation or countersinking 74 is provided at the guide opening 34 in the material in the vicinity of the atomizer disk 10 provided there. This lessens the capillary action in the annular gap of the guide opening 34 for the emerging droplets of medication during dosing. In other words, the distance for the emerging dosage droplet is smaller between the outlet opening 46 and the surface of the atomizer disk 10 than between the dosing opening 46 and the bottom of the indentation 74. As a result, the particle adhesion force of the atomizer disk 10 with respect to the droplet is reinforced, so that upon dosage it is assured that the droplet is placed on the surface of the atomizer disk 10, rather than in the vicinity of the annular gap at the opening 24, for example. A possible later return flow of the droplet of medication through a possible capillary action between the outer periphery of the cartridge tip and the guide opening of the upper part 2 is thus attained by means of a correspondingly enlarged guide opening diameter.

The lower and upper parts 2*a* and 2*b* can each be respectively composed of two halves or shells. This is shown in FIG. 4 for the lower part 2*a* by means of the seam line 76.

As already explained above, the upper part 2*b* can be mounted from above onto the lower part 2*a*, to which it can be snapped or clamped together with the aid of the detent closure 6. If the user then presses on the trigger 54, the back part 42*b* is forced into the front part 42*a* of the dosing cartridge 42, and a droplet of medication is expelled onto the atomizer disk 10. At the same time, the magnet 60 secured to the tongue 56 moves with the tongue toward the switch 14 and closes it. After the trigger 54 is released and the switch 14 opens, the switching process causes the droplet on the atomizer disk 10 to be atomized by ultrasonic vibration. It is converted into an aerosol that moves into the space 26. The aerosol can be inhaled by the user through the mouthpiece 30 (after the cap 32 is removed). During inhalation, air is aspirated through the air inlet opening 28. Due to the laminar flow effected by the screen plate 22, only slight settling of the medication onto the inner surfaces of the mouthpiece 30 in space 26 takes place. This is a considerable advantage in terms of operational reliability and hygiene.

It should also be stressed that in principle, the laminarizing means may instead be disposed in the upper part 2*b*, for example again in the form of a grid.

The foregoing is a description corresponding in substance to European Application 88 120 823.5, dated Dec. 13, 1988, the International priority of which is being claimed for the instant application, and which is hereby made part of this application. Any material discrepancies between the foregoing specification and the aforementioned corresponding European application are to be resolved in favor of the latter.

We claim:

1. Inhalator device, comprising:
a) a housing,
b) an ultrasonic atomizer disposed in said housing, said atomizer having an atomizer surface,
c) a cartridge for delivering a medication to said ultrasonic atomizer in said housing,
d) a mouthpiece disposed downstream of said ultrasonic atomizer in flow direction of the medication defining a space having walls between said ultrasonic atomizer and said mouthpiece,
e) said housing having an air inlet opening formed therein communicating with said space downstream of said ultrasonic atomizer, and
f) means disposed between said air inlet opening and said space for developing a laminar flow of aspirated air, said means being in the form of a perforated substantially flat wall having a multiplicity of relatively small holes disposed around at least a portion of the circumference of a relatively large opening formed in said substantially flat wall said atomizer surface being disposed coincidentally with said large opening, and said small holes being inclined towards said mouthpiece for avoiding formation of a film on said walls.

2. Inhalator according to claim 1, wherein said atomizer surface protrudes into said relatively large opening.

3. Inhalator according to claim 2, wherein said wall is inclined relative to said atomizer surface of said ultrasonic atomizer.

4. Inhalator according to claim 3, wherein said mouthpiece has an axis, and said wall is disposed in a plane being aligned at an angle of approximately 45° with respect to said axis.

5. Inhalator according to claim 1, wherein said air inlet opening has the shape of a slit.

6. Inhalator according to claim 1, wherein said air inlet opening is disposed above and in the immediate vicinity of said wall.

7. Inhalator according to claim 1, wherein said wall has an approximately half-ring shape.

8. Inhalator according to claim 1, wherein said housing includes a lower part and an upper part detachably secured to said lower part, said device for delivering a medication is disposed in said upper part, said mouthpiece is disposed on said upper part, said air inlet opening is formed in said lower part, and said ultrasonic atomizer and said means for developing a laminar flow of aspirated air are disposed in said lower part.

9. Inhalator according to claim 1, wherein said device for delivering a medication is a dosing cartridge being displaceable able into itself and having a front part with a dosing opening formed therein.

10. Inhalator according to claim 9, including means for firmly holding said dosing opening in place relative to said ultrasonic atomizer during a dosage operation.

11. Inhalator according to claim 10, wherein said holding means are in the form of a stop to be engaged by said front part of said dosing cartridge.

12. Pocket inhalator, comprising:
a) a housing,
b) an ultrasonic atomizer disposed in said housing, said atomizer having an atomizer surface,
c) a device for delivering a medication to said ultrasonic atomizer,
d) a mouthpiece disposed downstream of said ultrasonic atomizer in flow direction of the medication defining a space having walls between said ultrasonic atomizer and said mouthpiece,
e) said housing having an air inlet opening formed therein communicating with said space downstream of said ultrasonic atomizer, and
f) means disposed between said air inlet opening and said space for developing a laminar flow of aspirated air, said means being in the form of a perforated substantially flat wall having a multiplicity of relatively small holes disposed around at least a portion of the circumference of a relatively large opening formed in said substantially flat wall said atomizer surface being disposed coincidentally with said large opening, said holes being inclined towards said mouthpiece for avoiding formation of a film on said walls.

13. Inhalator device, comprising an ultrasonic atomizer having an atomizer surface, means for delivering a medication to said ultrasonic atomizer, outlet means disposed downstream of said ultrasonic atomizer in travel direction of a flow of the medication, and means disposed downstream of said ultrasonic atomizer for delivering air to the flow of the medication, said air delivering means being in the form of a perforated substantially flat wall having a multiplicity of relatively small holes disposed around at least a portion of the circumference of a relatively large opening formed in said substantially flat wall, said atomizer surface being disposed coincidentally with said large opening.

* * * * *